US00PP31146P3

(12) United States Plant Patent
Yoshioka et al.

(10) Patent No.: US PP31,146 P3
(45) Date of Patent: Dec. 3, 2019

(54) ***CITRUS L.* PLANT NAMED 'ASUKI'**

(50) Latin Name: *Citrus L.*
Varietal Denomination: ASUKI

(71) Applicant: NATIONAL AGRICULTURE AND FOOD RESEARCH ORGANIZATION, Tsukuba-shi (JP)

(72) Inventors: Terutaka Yoshioka, Tsukuba (JP); Toshio Yoshida, Tsukuba (JP); Hirohisa Nesumi, Tsukuba (JP); Satoshi Ota, Tsukuba (JP); Masayuki Kita, Tsukuba (JP); Takeshi Kuniga, Tsukuba (JP); Mutsuko Nonomura, Tsukuba (JP); Naoko Nakajima, Tsukuba (JP); Hiroko Hamada, Tsukuba (JP); Keisuke Nonaka, Tsukuba (JP); Fumitaka Takishita, Tsukuba (JP)

(73) Assignee: National Agriculture and Food Research Organization, Tsukuba-shi (JP)

( * ) Notice: Subject to any disclaimer, the term of this patent is extended or adjusted under 35 U.S.C. 154(b) by 0 days.

(21) Appl. No.: 15/998,043

(22) Filed: Jun. 19, 2018

(65) Prior Publication Data

US 2018/0368300 P1 Dec. 20, 2018

(30) Foreign Application Priority Data

Jun. 19, 2017 (JP) ..... 32235

(51) Int. Cl.
*A01H 5/08* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./201
See application file for complete search history.

*Primary Examiner* — Annette H Para
(74) *Attorney, Agent, or Firm* — Oblon, McClelland, Maier & Neustadt, L.L.P.

(57) ABSTRACT

A new and distinct variety of *Citrus L.* plant named 'ASUKI', characterized by being late-maturing, having high brix and excellent taste, being easy to eat because of its soft segment membrane, having no occurrence of fruit rind puffing, and having less dripping of fruit juice.

9 Drawing Sheets

The Latin name of the genus and species of the novel variety disclosed herein is: *Citrus L.*

The novel variety of the *Citrus L.* disclosed herein has been given the variety denomination: 'ASUKI'.

CROSS-REFERENCE TO RELATED APPLICATIONS

This application claims the benefit of Japanese Plant Breeder's Rights Application No. 32235 filed Jun. 19, 2017, which is incorporated by reference herein as if set forth in its entirety.

BACKGROUND OF THE INVENTION

The present invention relates to a new and distinct hybrid variety of *Citrus L.*, which was obtained in May 1992, from the cross between the 'KANKITSU OKITSU 46' (mother plant, undisclosed breeding material) and the 'HARUMI' (father plant, Japanese Variety Registration No. 7506, registered on Nov. 25, 1999), which was carried out in Okitsu-town, Shimizu-ward, Shizuoka-city, Shizuoka-prefecture, Japan. The hybrid seeds were collected in November 1992, and immediately sown in a glasshouse to grow hybrid seedlings. The seedlings were grafted on satsuma mandarin inter-stocks in April 1994, and first fruits were observed in 1997.

After the first fruiting, tests for fruits quality were carried out on the above-mentioned individuals grafted on satsuma mandarin inter-stocks, and among these, No. P-92 was first selected as the best individual in 2005, based on its high brix and excellent fruits quality. The No. P-92 was phylogenetically named as 'KANKITSU OKITSU 60' (which was varietally denominated as 'ASUKI' at a later date), and subjected to the national trial in 29 test sites in Japan, from April 2006. As a result of the above-mentioned national trial, on August 2016, it was evaluated that 'ASUKI' matured around medium to late March, and had high brix and extremely excellent taste stably every year, in almost all the test sites.

SUMMARY OF THE INVENTION

The present invention relates to a new and distinct variety of *Citrus L.* plant named 'ASUKI', as described and illustrated herein. Specifically, 'ASUKI' is a new and distinct variety of *Citrus L.*, characterized by being late-maturing, having high brix and excellent taste, being easy to eat because of its soft segment membrane, having no occurrence of fruit rind puffing, and having less dripping of fruit juice.

BRIEF DESCRIPTION OF THE FIGURES

The accompanying colored photographs (FIGS. 1-9) show typical tree, flower and fruit characteristics for the new

*Citrus L.* plant, 'ASUKI'. Colors shown are as accurate as can be reasonably reproduced by photographic means. In some cases, the color might differ slightly from the colors of 'ASUKI' recited in the description.

DETAILED DESCRIPTION OF THE VARIETY

Figure 1:
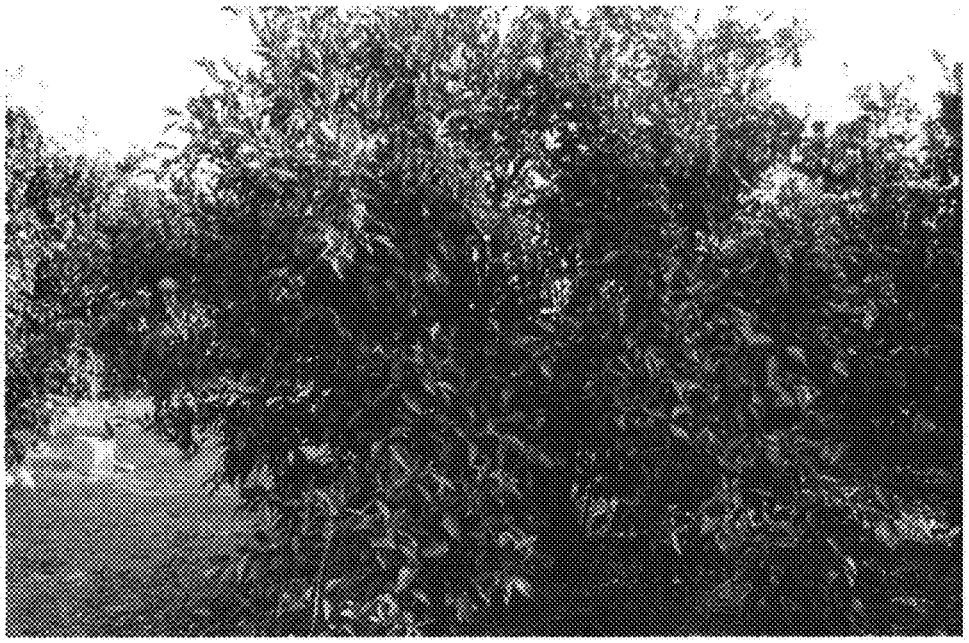
FIG. 1 shows a tree of *Citrus L.* plant 'ASUKI' (photographed date: Mar. 13, 2015; photographed location: Okitsu-town, Shimizu-ward, Shizuoka-city, Shizuoka-prefecture, Japan; and the age of photographed 'ASUKI': 15 years).
Figure 2:
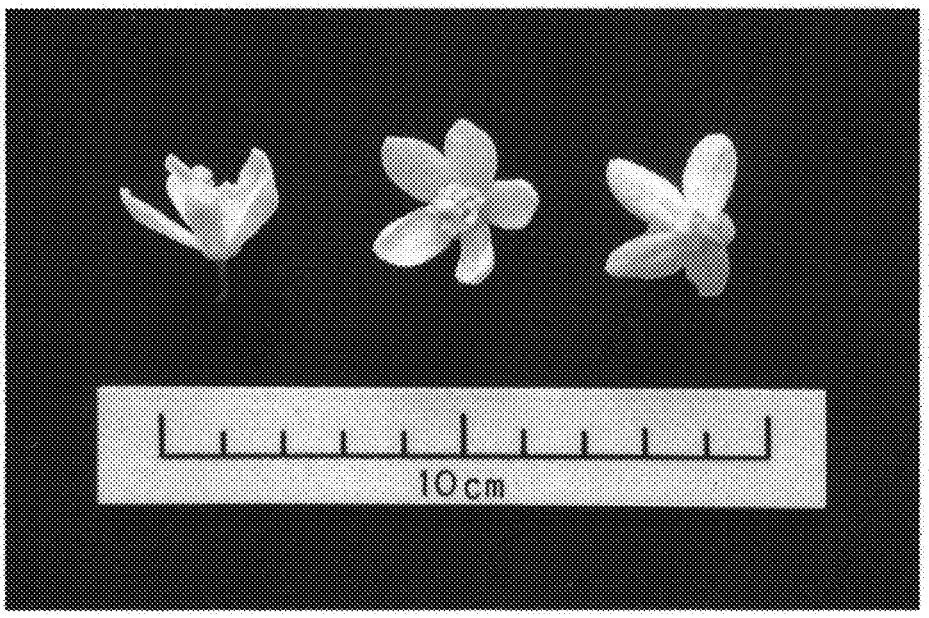
FIG. 2 shows whole flowers of *Citrus L.* plant 'ASUKI' (photographed date: May 12, 2015; photographed location: same as FIG. 1; and the age of photographed 'ASUKI': 15 years).
Figure 3:
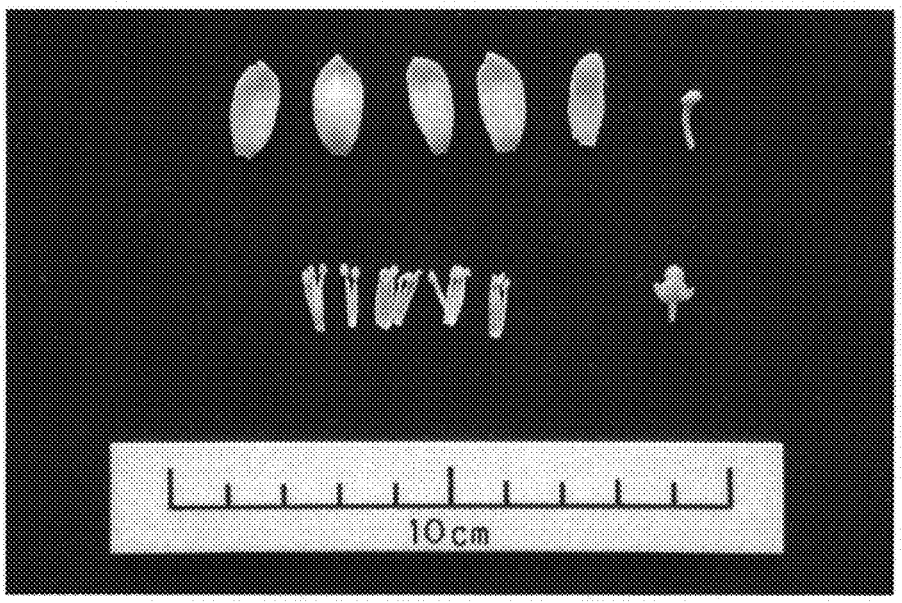
FIG. 3 shows broken-down parts of the flower of *Citrus L.* plant 'ASUKI' (photographed date: May 12, 2015; photographed location: same as FIG. 1; and the age of photographed 'ASUKI': 15 years).
Figure 4:
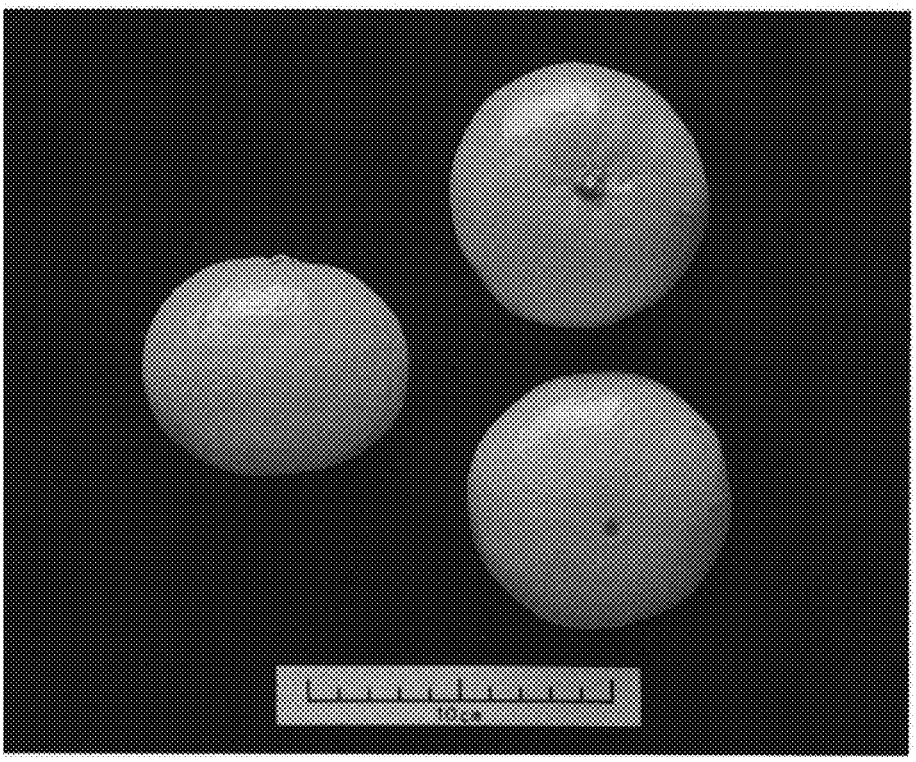
FIG. 4 shows whole fruits of *Citrus L.* plant 'ASUKI' (photographed date: Mar. 5, 2015; photographed location: same as FIG. 1; and the age of photographed 'ASUKI': 15 years).
Figure 5:
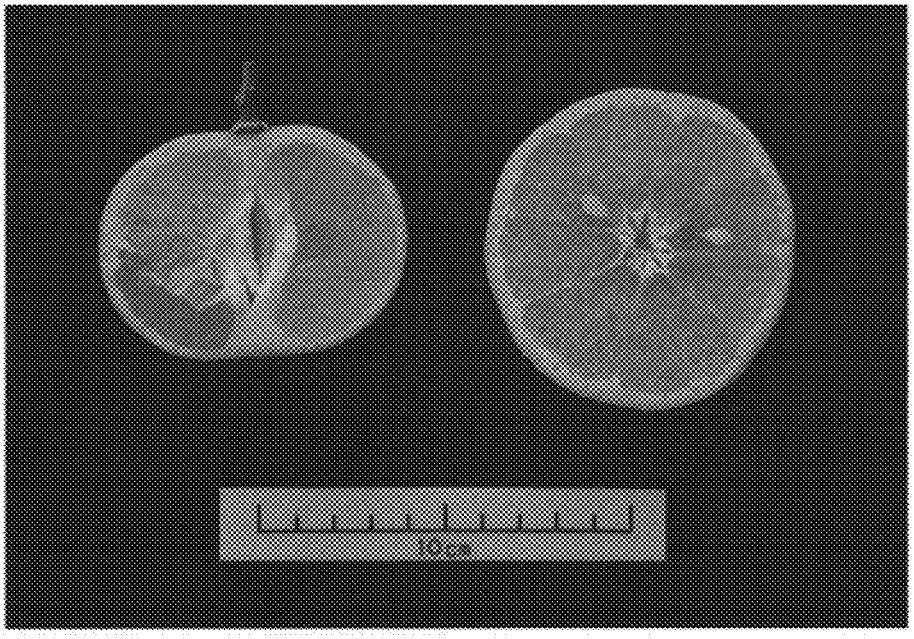
FIG. 5 shows a longitudinal and a horizontal section of whole fruits of *Citrus L.* plant 'ASUKI' (photographed date: Mar. 5, 2015; photographed location: same as FIG. 1; and the age of photographed 'ASUKI': 15 years).
Figure 6:
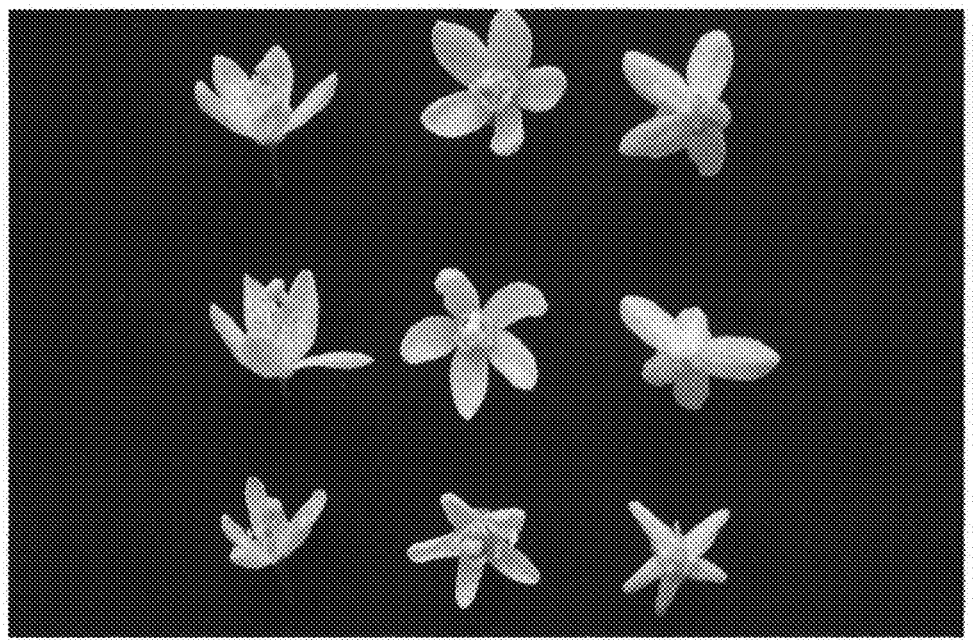
FIG. 6 shows a comparison of flowers of 'ASUKI' with those of 'ASUMI' and 'SETOKA' (both of which are varieties morphologically similar to 'ASUKI' in terms of fruit). Upper: 'ASUKI', medium: 'ASUMI', lower: 'SETOKA' (photographed date: May 12, 2015; photographed location: same as FIG. 1; and the age of photographed 'ASUKI': 15 years).
Figure 7:
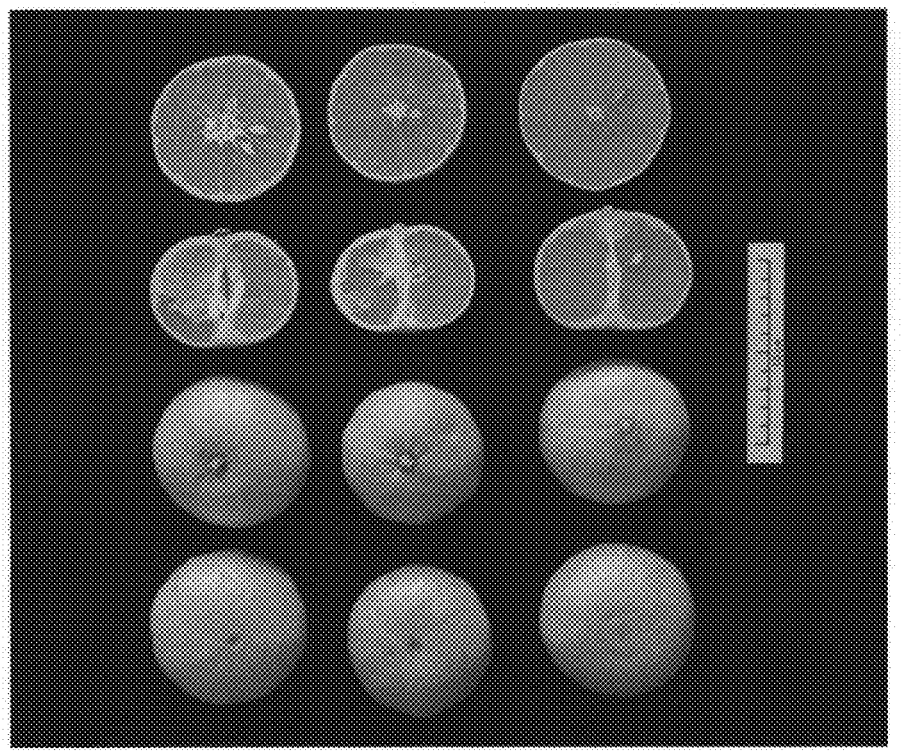
FIG. 7 shows a comparison of fruits of 'ASUKI' with those of 'ASUMI' and 'SETOKA'. Left: 'ASUKI', medium: 'ASUMI', right: 'SETOKA' (photographed date: Mar. 5, 2015; photographed location: same as FIG. 1; and the age of photographed 'ASUKI': 15 years).
Figure 8:
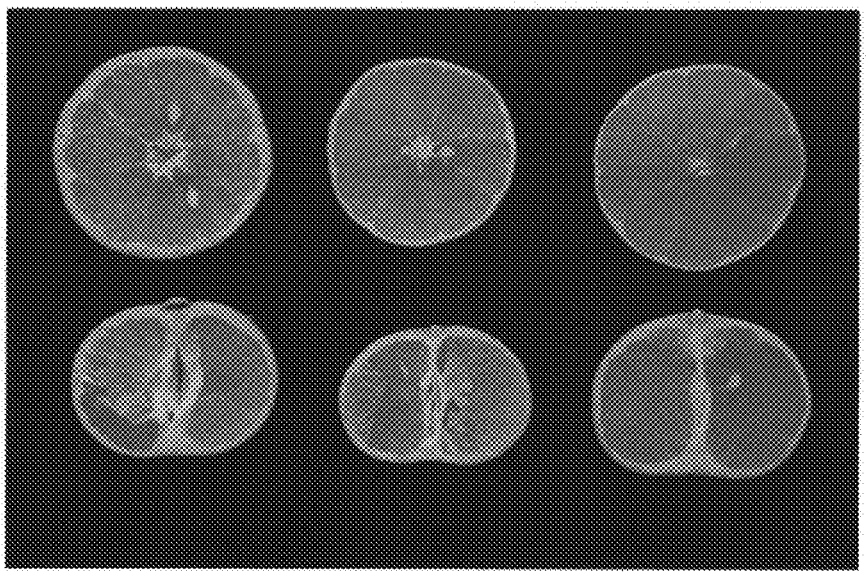
FIG. 8 shows a comparison of thicknesses of fruit rind of 'ASUKI' with those of 'ASUMI' and 'SETOKA'. Left: 'ASUKI', medium: 'ASUMI', right: 'SETOKA'. Thickness of fruit rind of 'ASUKI': thin, 'ASUMI' and 'SETOKA': extremely thin (photographed date: Mar. 5, 2015; photographed location: same as FIG. 1; and the age of photographed 'ASUKI': 15 years).
Figure 9:
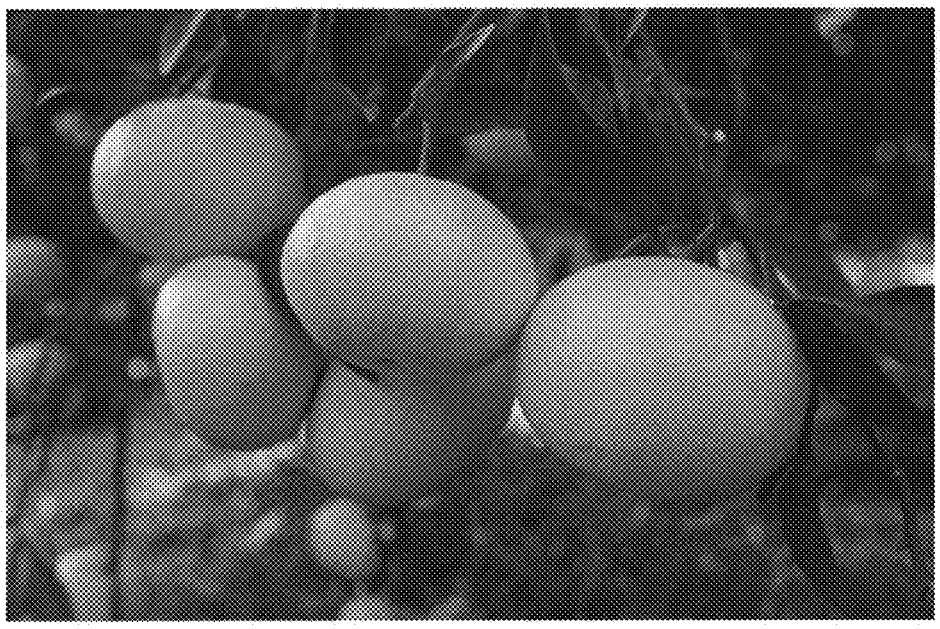
FIG. 9 shows fruits on a tree of 'ASUKI' (photographed date: Mar. 13, 2015; photographed location: same as FIG. 1; and the age of photographed 'ASUKI': 15 years).

The following is a detailed description of the new *Citrus L.* variety known as 'ASUKI', based upon the traits evaluated in each test sites in Japan.

As described above, 'ASUKI' was obtained from the cross between 'KANKITSU OKITSU 46' as a mother plant and 'HARUMI' as a father plant. The applicants had asexually reproduced 'ASUKI' by grafting it onto trifoliate orange rootstocks in Okitsu-town, Shimizu-ward, Shizuoka-city, Shizuoka-prefecture, Japan, and from 2013 to 2015, the traits evaluation of 'ASUKI' was carried out by being compared with other *Citrus L.* varieties 'ASUMI' (Japanese variety registration No. 23723, registered on Sep. 30, 2014) and 'SETOKA' (Japanese variety registration No. 9398, registered on Oct. 18, 2001)(both of which are varieties morphologically similar to 'ASUKI' in terms of fruit) as well as 'AOSHIMAUNSHIU' and 'SHIRANUI' (both of which are leading *Citrus* varieties in Japan). The results of the traits evaluation were as follows. The plant age of all the plants of 'ASUKI' was 15 years. In addition, the growing conditions of these plants were the following: (a) the annual rainfall in the observed area (Skizuoka-city, Shizuoka-prefecture, Japan) was 1800 mm to 2700 mm (more than 200 mm per month in March to October, and less than 100 mm per month in November to February, which corresponds to maturation season of the fruits of 'ASUKI'); (b) the annual sunshine in hours in the observed area was about 2000 hours per year; (c) the average annual temperature in the observed area was 16 to 17° C. (the highest temperature: 37° C. and the lowest temperature: −3.8° C.); and (d) the soil property in the observed field was fertile brown forest soil, including compost.

(1) Tree Characteristics

The tree vigor of 'ASUKI' was slightly stronger than those of 'SETOKA', 'AOSHIMAUNSHIU' and 'SHIRANUI'. The color of tree bark of 'ASUKI' was Strong Yellowish Brown N199D (The R.H.S. Colour Chart). The tree shape of 'ASUKI' was spheroid to ellipsoid, and the growth habit was upright to spreading. The average trunk circumference of 'ASUKI' was 77 cm (n=5), the average trunk diameter of 'ASUKI' was 12.5 cm (n=5), and the trunk surface texture of 'ASUKI' was slightly smooth without pitting. The shoot length of 'ASUKI' was long (for example, average length of shoot: about 13.5 cm, n=30), and the diameter (for example, about 2.9 mm) and density of shoots were medium. The internode length of 'ASUKI' was medium (for example, average length of internode: about 1.9 cm, n=30). The percentage of occurrence of thorns on shoots was low (8%, n=30), so that the density of thorns on shoots was sparse, and in some years, there was almost no occurrence of thorn. The length of thorns on shoots of 'ASUKI' were short (Table 1).

TABLE 1

Numbers and length of 'ASUKI' thorns

| | Year | | | |
|---|---|---|---|---|
| | 2013 | | 2014 | |
| Variety | Number | Length | Number | Length |
| ASUKI | medium | short | none | |
| ASUMI | — | — | many | short |
| SETOKA | medium | short | many | short |
| AOSHIMAUNSHIU | none | | none | |
| SHIRANUI | none | | none | |

| | Year | | Evaluation | |
|---|---|---|---|---|
| | 2015 | | through three years | |
| Variety | Number | Length | Number | Length |
| ASUKI | few | short | none to few | short |
| ASUMI | many | medium | many | short to medium |
| SETOKA | many | short | medium to many | short |

TABLE 1-continued

| Numbers and length of 'ASUKI' thorns | | |
|---|---|---|
| AOSHIMAUNSHIU | none | none |
| SHIRANUI | none | none |

—: not investigated
Numbers of thorns were observed including summer and fall shoots.
none: without thorn.
few: intermediate (there were thornless parts on shoots).
many: thorns occurred on most shoots.
Length of thorns were observed on average spring shoots.
short: less than 1 cm.
medium: 1 to 2 cm.
long: no less than 2 cm.

The shape of leaf blade of 'ASUKI' was lanceolate, just like those of 'ASUMI' and 'SETOKA', and the length (for example, average length of leaf: about 9.2 cm, n=30) and the size (for example, about 25.3 $cm^2$) of leaf blade was medium, and the width of leaf blade was narrow (for example, average width of leaf: about 3.8 cm, n=30). The thickness of leaf of 'ASUKI' (for example, about 0.37 mm) was at the same level as those of 'ASUMI' and 'SETOKA'. The color of upper surface of leaf of 'ASUKI' was Moderate Olive Green 137A (The R.H.S. Colour Chart), and the color of lower surface of leaf of 'ASUKI' was Moderate Yellow Green 146B (The R.H.S. Colour Chart). The petiole wings of 'ASUKI' was wedge shaped, and its length (for example, average length of petiole wings: about 14.7 mm, n=30) was medium and its width (for example, average width of petiole wings: about 3.7 mm, n=30) was narrow. The length of petiole of 'ASUKI' was medium (for example, average length of petiole: about 18.7 mm, n=30), and its diameter was wide (for example, average diameter of petiole: about 2.0 mm, n=30). The weight of a flower (for example, about 0.44 g) and the size of a petal (for example, length: about 14.5 mm; width: about 7.2 mm) of 'ASUKI' were smaller than those of 'ASUMI', and larger than those of 'SETOKA'. The flower of 'ASUKI' did not have inflorescence and was solitary. The color of flower petals of 'ASUKI' was white, and one flower had 5 petals. The color of opened flower of 'ASUKI' was White NN155D (The R.H.S. Colour Chart). The number of flower filaments of 'ASUKI' was few (for example, about 18.8) and the filaments were separated from each other. The amount of pollen of 'ASUKI' was at the same level as that of 'ASUMI', and larger than that of 'SETOKA'. The flower's style of 'ASUKI' was arched, and the curvature degree of the style was lower than that of 'ASUMI'.

The number of flower setting of 'ASUKI' was medium, and there was little preharvest drops. The alternate bearing of 'ASUKI' was lighter than those of 'ASUMI' and 'SETOKA', and the yielding ability of 'ASUKI' was medium. The degree of occurrence of *Citrus* canker disease was lower than those of 'ASUMI' and 'SETOKA'. There was no occurrence of *Citrus* scab on 'ASUKI' under conventional control (Table 2).

TABLE 2

Degree of occurrence of 'ASUKI' plant diseases

| | Year | | | |
|---|---|---|---|---|
| | 2013 | | 2014 | |
| Variety | citrus conker | citrus scab | citrus canker | citrus scab |
| ASUKI | none | none | none | none |
| ASUMI | none | none | slight | none |
| SETOKA | none | none | slight | none |
| AOSHIMAUNSHIU | none | none | none | none |
| SHIRANUI | none | none | none | none |

| | Year | | | |
|---|---|---|---|---|
| | 2015 | | Evaluation through three years | |
| Variety | citrus canker | citrus scab | citrus canker | citrus scab |
| ASUKI | none | none | none | none |
| ASUMI | slight | none | none to slight | none |
| SETOKA | slight | none | none to slight | none |
| AOSHIMAUNSHIU | none | none | none | none |
| SHIRANUI | none | none | none | none |

citrus canker disease, citrus scab: degree of damages on fruits and trees under conventional control. none: no symptom was observed. slight: some pathological spots were observed, but no problem fix cultivation. moderate: intermediate. severe: a lot of pathological spots appeared, and there is a problem on cultivation.

(2) Fruit Characteristics

The time of sprouting of 'ASUKI' (early April) was almost the same as those of 'ASUMI' and 'SETOKA', and the full bloom stage of 'ASUKI' (early May) was at the same time as those of 'ASUMI' and 'SETOKA'. While the beginning time of fruit coloration of 'ASUKI' (middle October) was at the same time as that of 'ASUMI', it was 10 to 15 days later than those of 'SETOKA' and 'AOSHIMAUNSHIU'. The time of complete coloring of fruits of 'ASUKI' was late (latter half of December), and it was at the same level as 'ASUMI'. The time of maturing of fruits of 'ASUKI' was late February to March, and it was more than 1 month later than that of 'ASUMI' (Table 3).

TABLE 3

Maturing time of 'ASUKI' fruits

| | Year | | | Evaluation through |
|---|---|---|---|---|
| Variety | 2013 | 2014 | 2015 | three years |
| ASUKI | early March | early March | late February | late February to March |
| ASUMI | early February | late January | late January | late January to early February |
| SETOKA | late February | late February | late February | late February |
| AOSHIMAUNSHIU | — | early December | late November | late November to early December |
| SHIRANUI | — | late February | late February | late February |

: not investigated
Maturing time of fruits: determined by progress degree of coloration and fruit quality.

The fruit shape of 'ASUKI' was oblate in form, the color of fruit rind (skin of fruit) of 'ASUKI' was Vivid orange 28B (The R.H.S. Colour Chart), and the surface of fruit was smooth. The average thickness of fruit rind of 'ASUKI' was about 2.7 mm (n=15) and it was thicker than those of 'ASUMI' and 'SETOKA', and 'ASUKI' was easier to be peeled than 'ASUMI'. The fruit rind of 'ASUKI' had orange-like flavor. The color of fruit flesh of 'ASUKI' was Strong Orange 169B (The R.H.S. Colour Chart), and the pulp rate was relatively high (for example, about 82.6%). The segment membrane of 'ASUKI' was relatively thin and soft, and the fruit flesh texture was medium to slight firm. The external color of seed of 'ASUKI' was Pale Yellow 160D (The R.H.S. Colour Chart), and the color of inner seed coat of 'ASUKI' was Moderate Yellow 161A (The R.H.S. Colour Chart). The average fruit weight of 'ASUKI' was about 180 g, (n=15), and it was at the same level as those of 'ASUMI' and 'SETOKA'.

The brix of fruit juice of 'ASUKI' was more than 15% around February 20, and it was increased up to about 16% around March 20, and was higher than those of 'ASUMI' and 'SETOKA'. The acid content of fruit juice of 'ASUKI' was about 1.18 g/100 ml around March 20, and the fruit of 'ASUKI' had extremely rich taste (Table 4).

TABLE 4

Fruit characteristics of 'ASUKI'

| | Year | | | | | |
|---|---|---|---|---|---|---|
| | investi- | 2013 | | | | |
| Variety | gation date Month. Day | Weight of fruit g | Brix % | Acid content g/100 ml | Bitter-ness | 2014 Weight of fruit g |
| ASUKI | 2.20 | 172 | 16.1 | 1.57 | none | 171 |
| | 3.20 | 165 | 16.8 | 1.33 | none | 176 |
| ASUMI | 2.20 | 161 | 14.3 | 1.10 | none | 173 |
| SETOKA | 2.20 | 194 | 14.4 | 1.42 | none | 176 |
| AOSHIMA-UNSHIU | 11.20 | 166 | 9.5 | 0.70 | none | 168 |
| SHIRANUI | 2.20 | 220 | 15.9 | 1.33 | none | 277 |

| | Year | | | | | |
|---|---|---|---|---|---|---|
| | 2014 | | | 2015 | | |
| Variety | Brix % | Acid content g/100 ml | Bitter-ness | Weight of fruit g | Brix % | Acid content g/100 ml |
| ASUKI | 15.7 | 1.48 | none | 200 | 15.1 | 1.05 |
| | 15.7 | 1.18 | none | 187 | 15.7 | 1.03 |
| ASUMI | 14.0 | 0.93 | none | 185 | 15.0 | 0.68 |
| SETOKA | 13.6 | 1.53 | none | 195 | 13.8 | 1.19 |
| AOSHIMA-UNSHIU | 9.7 | 0.81 | none | 154 | 9.9 | 0.78 |
| SHIRANUI | 14.2 | 1.04 | none | 281 | 14.7 | 0.90 |

| | Year | | | | |
|---|---|---|---|---|---|
| | | Evaluation through three years | | | |
| Variety | 2015 Bitter-ness | Weight of fruit g | Brix % | Acid content g/100 ml | Bitter-ness |
| ASUKI | none | 181 | 15.6 | 1.37 | none |
| | none | 176 | 16.1 | 1.18 | none |
| ASUMI | none | 173 | 14.4 | 0.97 | none |
| SETOKA | none | 188 | 13.9 | 1.38 | none |
| AOSHIMA-UNSHIU | none | 163 | 9.7 | 0.76 | none |
| SHIRANUI | none | 259 | 14.9 | 1.09 | none |

The fruit of 'ASUKI' was tight and there was no occurrence of fruit rind puffing. And also, there was neither occurrence of fruit cracking nor physiological granulation (Table 5).

TABLE 5

Occurrence of physiological disorder on 'ASUKI' fruits

| | Year | | | |
|---|---|---|---|---|
| | 2013 | | | |
| Variety | Rind puffing | Cracking | Granu-lation | Others |
| ASUKI | none | none | none | slight: sunacald |
| ASUMI | none | slight | none | |
| SETOKA | none | none | none | |
| AOSHIMAUNSHIU | medium | none | none | |
| SHIRANUI | little | none | none | |

| | Year | | | |
|---|---|---|---|---|
| | 2014 | | | |
| Variety | Rind puffing | Cracking | Granu-lation | Others |
| ASUKI | none | none | none | slight: sunacald |
| ASUMI | none | slight | none | |
| SETOKA | none | slight | none | |
| AOSHIMAUNSHIU | little | none | none | |
| SHIRANUI | little | none | none | |

| | Year | | | |
|---|---|---|---|---|
| | 2015 | | | |
| Variety | Rind puffing | Cracking | Granu-lation | Others |
| ASUKI | none | none | none | slight: sunacald |
| ASUMI | none | slight | none | |
| SETOKA | none | slight | none | |
| AOSHIMAUNSHIU | much | none | none | |
| SHIRANUI | little | none | none | |

Rind puffing was numeralized as follows: none: no occurrence of rind puffing (score 0), little: rind was puffed around pedicel (score 1), medium: rind puffing was reached to equatorial portion of fruit (score 2), and much: rind was puffed throughout whole fruit (score 3), and evaluated by their average valule.
Cracking of fruits were based on observation.
none: without craking fruit.
slight: less than 10% of fruits were craking fruits.
many: no less than 10% of fruits were craking fruits.
Granulation of fruits were based on observation.
none: no granulation was observed.
slight: slight granulations were observed.
moderate: granulations were apparently observed, but not greater than ¼ of fruit pulps.
severe: no less than ¼ of fruit pulps were granulated.
When another physiological disorder was present, the type and degree of the physiological disorder was described.
slight: some physiological disorder were found, but no problem for production of fruits.
severe: there is a problem on production of fruits.

When being cut by knife, the degree of dripping of fruit juice of 'ASUKI' was lower than those of Grapefruit (*Citrus paradisi*), Kawano-natsudaidai orange (*Citrus natsudaidai f. kawanonatsudaidai*) etc. (see Table 6 below), and was almost the same level as that of Sweet Orange (*Citrus sinensis*), so that 'ASUKI' is suitable for being used as cut fruits.

TABLE 6

Degree of fruit juice dripping of 'ASUKI'

| Investigation month | Variety Name | The amount of fruit juice dripping after storage* (g) | The amount of fruit juice dripping immediately after cutting of fruit** (mg) |
|---|---|---|---|
| 2 | Orange (*Citrus sinensis*) | 0.527 | 6.87 |
| 3 | ASUKI (*Citrus L.*) | 0.562 | 4.25 |
| 2 | ASUKI (*Citrus L.*) | 0.655 | 3.85 |
| 4 | KAWANONATSUDAIDAI (*Citrus natsudaidai Hayata f. Kawanonatsudaidai*) | 1.189 | 9.69 |
| 2 | Grapefruit (*Citrus paradisi*) | 1.384 | 12.25 |
| 12 | AOSHIMAUNSHIU (*Citrus unshiu*) | 1.444 | 5.57 |

TABLE 6-continued

Degree of fruit juice dripping of 'ASUKI'

| Investigation month | Variety Name | The amount of fruit juice dripping after storage* (g) | The amount of fruit juice dripping immediately after cutting of fruit** (mg) |
|---|---|---|---|
| 3 | KIYOMI (*Cirrus unshiu* x *Citrus sinensis*) | 1.847 | 4.83 |

*The amount of fruit juice dripping per 100 g of fruit pulp, after sealed storage at 4° C. for 24 hour.
**The amount of fruit juice dripping per cross section (1 $cm^2$).

What is claimed is:

1. A new and distinct variety of *Citrus L.* plant named 'ASUKI', as described and illustrated herein.

* * * * *